(12) United States Patent
Kamran et al.

(10) Patent No.: US 8,257,443 B2
(45) Date of Patent: Sep. 4, 2012

(54) OPEN BODY BOX FORM INTERBODY FUSION CAGE

(76) Inventors: Aflatoon Kamran, Corona del Mar, CA (US); Chris Maurer, Wakefield, MA (US)

( * ) Notice: Subject to any disclaimer, the term of this patent is extended or adjusted under 35 U.S.C. 154(b) by 247 days.

(21) Appl. No.: 12/660,153

(22) Filed: Feb. 19, 2010

(65) Prior Publication Data

US 2011/0054616 A1 Mar. 3, 2011

Related U.S. Application Data

(60) Provisional application No. 61/208,000, filed on Feb. 19, 2009.

(51) Int. Cl.
*A61F 2/44* (2006.01)
(52) U.S. Cl. .................................. 623/17.16
(58) Field of Classification Search ..... 623/17.11–17.16
See application file for complete search history.

(56) References Cited

U.S. PATENT DOCUMENTS

| | | | | |
|---|---|---|---|---|
| 4,636,217 A | * | 1/1987 | Ogilvie et al. | 623/17.11 |
| 7,846,188 B2 | * | 12/2010 | Moskowitz et al. | 606/279 |
| 2005/0049590 A1 | * | 3/2005 | Alleyne et al. | 606/61 |
| 2006/0069436 A1 | * | 3/2006 | Sutton et al. | 623/17.13 |
| 2010/0160984 A1 | * | 6/2010 | Berry et al. | 606/86 A |
| 2010/0161057 A1 | * | 6/2010 | Berry et al. | 623/17.16 |

* cited by examiner

*Primary Examiner* — Ellen C Hammond
(74) *Attorney, Agent, or Firm* — Ober, Kaler, Grimes & Shriver; Royal W. Craig; Christopher F. Lonegro

(57) ABSTRACT

An interbody fusion cage having a generally symmetric, annular cage body surrounding a central void extending from a lower surface to an upper surface in which to retain graft material in contact with adjacent vertebra. A lateral channel extending into each half from the cage perimeter contains a worm drive screw. One or more longitudinal channels extending from the upper surface to the lower surface intersect each lateral channel and house a pin which is provided with a series of helically cut worm gear teeth on its external surface for engaging the worm drive screw. The pins are simultaneously externally threaded and engaged to the cooperatively threaded internal surface of the longitudinal channel such that rotation of the drive screw by the surgeon after implantation causes the pins to rotate with the longitudinal channel and advance into the adjacent bone.

14 Claims, 5 Drawing Sheets

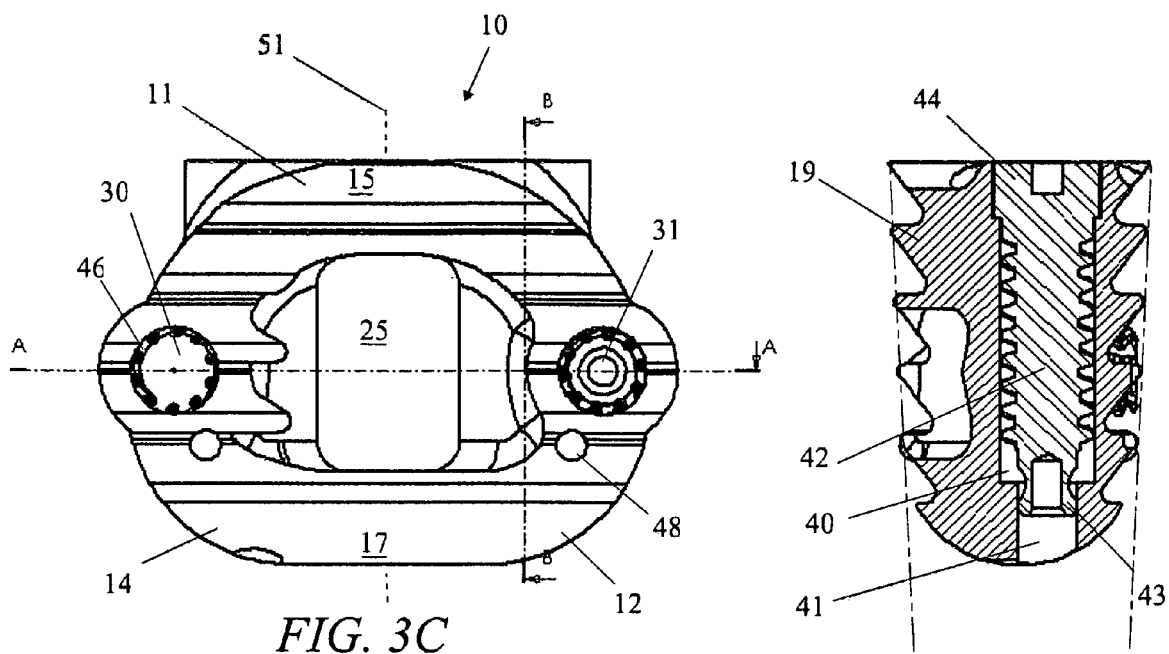
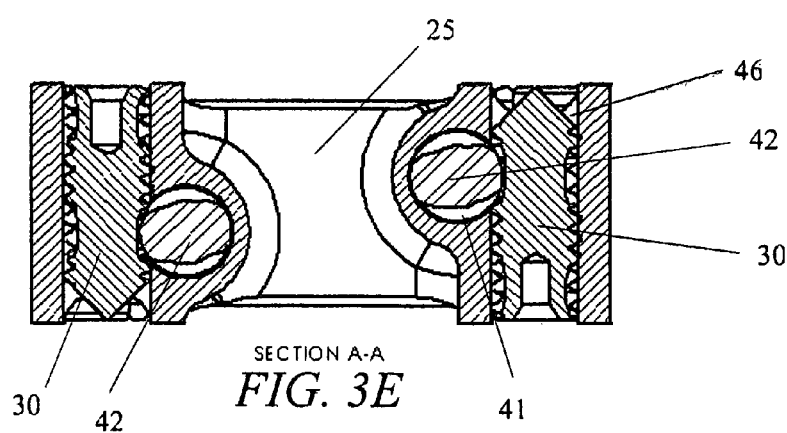
FIG. 3C
FIG. 3F
FIG. 3E
SECTION A-A

OPEN BODY BOX FORM INTERBODY FUSION CAGE

CROSS-REFERENCE TO RELATED APPLICATIONS

The present application derives priority from U.S. Provisional Patent Application 61/208,000 for an "Open Body Box Form Interbody Fusion Cage" filed Feb. 19, 2009 which is further incorporated herein by reference.

BACKGROUND OF THE INVENTION

1. Field of the Invention

The present invention relates generally to devices and methods for treating spinal disorders and more specifically to an intervertebral device for aligning and maintaining the relative position of two or more adjacent vertebrae as well as to contain graft material to facilitate immobilization of the vertebra through fusion to eliminate the pain caused by abnormal motion.

2. Description of the Background

Degeneration of the intervertebral discs and the concomitant instability and translocation of the vertebra is a common cause of back pain and may result from a variety of problems including congenital deformity, age related degeneration, osteoporosis, tumor and disc herniation as a result of trauma. Disc degeneration, for whatever reason, results in compression of the spinal nerve roots resulting in pain. Palliative care is often successful in mild cases but more extreme or degenerative cases may require a surgical approach to stabilize the joint and relieve pressure.

A number of surgical approaches have been developed with varying degrees of success depending on the cause and severity of the damage. A ruptured disc impinging the nerve root may be partially excised to relieve pressure. In such a case the adjacent vertebra may be further fixated using rods, screws and plates in an attempt to stabilize the spine and delay or prevent further degeneration. Patients undergoing such excisions and fixations however often require subsequent procedures to address recurrent pain. In many case such subsequent procedures include fusion. Spinal fusion, or spondylosyndesis, is a surgical technique to combine two or more vertebrae utilizing supplementary bone graft tissue in conjunction with the body's natural osteoblastic processes to eliminate relative movement as a source of pain. A variety of approaches to fusion are available including posterior fusion, postero-lateral fusion and anterior or posterior interbody fusion.

In the more traditional posterior fusion approach, performed in conjunction with partial excision of the ruptured disc, growth is induced between the bony vertebral laminae to fix the position of the vertebra. In the postero-lateral fusion method bone growth is induced to join the transverse processes to prevent motion between the adjacent vertebrae. However, both posterior and postero-later fusion tends to cause bony overgrowth leading to nerve root compression and pain by spinal stenosis. This, coupled with other risks, limitations and disappointing fusion success rates have caused surgeons searching for alternate fusion means to develop interbody fusion techniques.

Interbody fusion techniques involve complete excision of the soft disc which is then replaced with autograft material harvested from the patient, prepared allograft from a donor source or, more recently, bone morphogenic protein. Most commonly performed in the lumbar region the procedure can be accomplished from an anterior approach (Anterior Lumbar Interbody Fusion or ALIF) or a posterior approach (PLIF). In either case the procedure attempts to reconstruct the normal anatomic relationships between the bony and the neural structures and has many advantages. Specifically, weight bearing through a solid bony fusion mass between vertebral bodies relieves the mechanical pain of the traditional unstable degenerative disc and generally prevents long term disc collapse or further degenerative changes. The complete disc excision prevents recurrent herniation of the same degenerated disc.

Successful fusion results in a contiguous growth of bone to create a solid mass that will unite the vertebra into one unit. When fusion graft material is first placed in the intervertebral space it is soft and lacking in cohesive strength so as to be incapable of remaining in position or carrying any load without assistance. A variety of appliances have been developed that attempt to hold the vertebrae to be joined in place relative to one another under normal spinal activity and daily stress to allow the fusion process to occur over the 18-24 month period generally required. Such appliance are often referred to as interbody cages and provide a mechanically rigid scaffold in which the graft material may be placed.

Cage designs vary widely but generally fall into one of three categories. Horizontal cylinders are generally made from titanium and inserted by either the posterior or anterior approach into complimentary holes bored into the intervertebral space. They can be placed by open or minimally invasive techniques. U.S. Pat. No. 5,026,373 to Ray, et al. discloses a cage of this design that includes a perforated threaded exterior surface that can be screwed into place between the vertebra and packed with bone material. Bone growth through the perforations and into the cancellous bone of the vertebra exposed by the insertion results in the desired fusion.

A second design in the form of a vertical cylinder or ring is often referred to as a Harms cage and is also typically made from titanium. The Harms cage can be cut to length as desired so as to span larger segments of the lumbar spine. End caps are employed to prevent subsidence into the cancellous bone although this design suffers, as a result, from a requirement that its central void be pack with graft material prior to insertion. Due to its sharp edges the Harms cage is most commonly inserted by open techniques. U.S. Pat. No. 5,989,290 to Biedermann et al, et al. discloses a cage of this design.

A third design form is the open box cage. Typically constructed of carbon, titanium or bio-compatible non-metallic materials, this design can be formed for an anatomical fit or to recreate the normal lumbar lordosis. Openings in the box walls permit graft material contained therein to contact the vertebral bone. Some designs utilize a single large cage. Alternately, a pair of smaller cages is utilized which can be inserted posteriorly using minimally invasive techniques. U.S. Pat. No. 6,241,769 to Nicolson et al, et al. discloses a box form cage having a central void having an open top and bottom and a dovetail system for structurally attaching the device to the adjacent vertebra which are prepared by cutting cooperative channels in their surface.

Cages provide enhanced mechanical stability prior to fusion, maintain the intervertebral disc height and ultimately provide a high rate of successful fusion. The ideal cage should rigidly immobilize the spine in all modes of articulation, be strong enough to withstand repeated loadings and have a modulus of elasticity similar to that of cortical bone. It should also be easy to insert by open or minimally invasive methods, resist subsidence, translation or retropulsion and be clinically effective.

It would be therefore an improvement in this art to provide an interbody fusion cage for facilitating vertebral fusion and thereby eliminating spinal back pain caused by ruptured or degenerated vertebral discs which overcomes the deficiencies of prior known devices. It is an object of the present invention to provide an interbody fusion cage of open form design that can easily be placed in the evacuated interbody space to constrain relative vertebral motion and which can subsequently be secured again translation aid retropulsion. It is a further object of the present invention to provide an interbody fusion cage that is sufficiently robust so as to withstand the forces imposed by normal daily activity on the part of the patient and which is clinically effective it retaining osteoconductive or osteoinductive material so as to facilitate fusion.

SUMMARY OF THE INVENTION

Accordingly, there is provided a box form interbody fusion cage including a cage body having a generally annular form around a central void extending from a lower surface to an upper surface in which to retain graft material in contact with upper and lower adjacent vertebra. The cage body is generally divisible into symmetric left and right halves about a midline with a lateral channel extending into each half from the cage perimeter. A worm drive screw is rotatably affixed within each lateral channel. A longitudinal channel extending from the upper surface to the lower surface partially intersects each lateral channel and houses a sharp pin. Each pin is provided with a series of helically cut worm gear teeth on its external surface for engaging the worm drive screw where the channels intersect within each half. The pins are simultaneously externally threaded and engaged to the cooperatively threaded internal surface of the longitudinal channel.

After implantation between adjacent vertebra to be fused, the drive screws, accessible through the sidewalls of the cage body, are turned by the surgeon using a tool to engage the screw head. Rotation of the worm drive screw in turn causes the pin to rotate with the longitudinal channel and advance through the upper of lower surface of the cage body and into the adjacent bone due to its threaded engagement with the channel wall. Multiple pins may be advanced by a single worm drive screw in order to stabilize the spine for fusion. The central void may be packed with graft material before or after implantation.

The foregoing objects, features and attendant benefits of this invention will, in part, be pointed out with particularity and will become more readily appreciated as the same become better understood by reference to the following detailed description of a preferred embodiment and certain modifications thereof when taken in conjunction with the accompanying drawings.

BRIEF DESCRIPTION OF THE DRAWINGS

In the drawings:

FIG. 3c is a top view of an interbody cage according to the present invention.

FIG. 3e is a sectional view through an embodiment according to the present invention.

FIG. 3f is a sectional view through an embodiment according to the present invention.

DETAILED DESCRIPTION OF THE PREFERRED EMBODIMENTS

Figure 1:
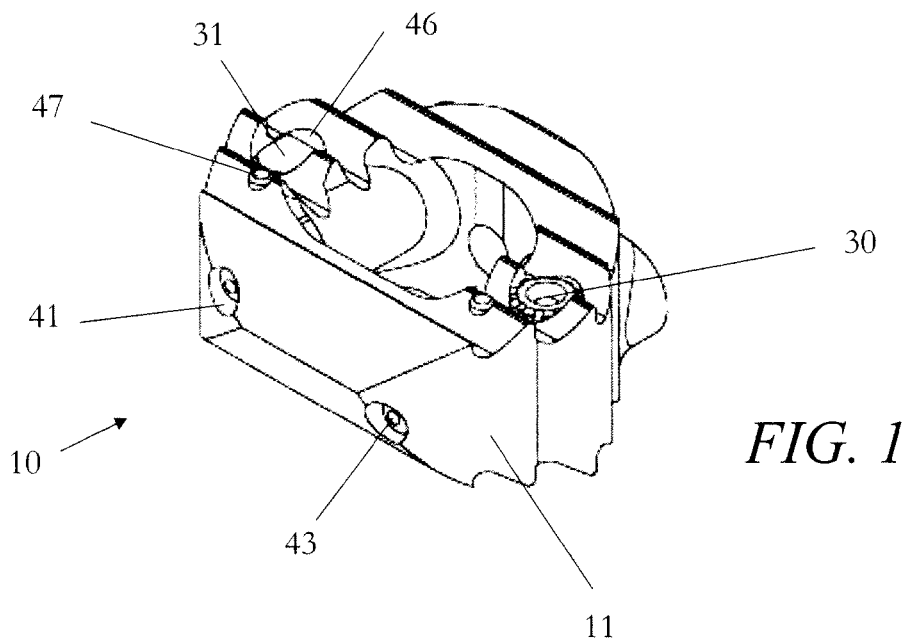
FIG. 1 is a perspective view of an embodiment according to the present invention.
Figure 2:
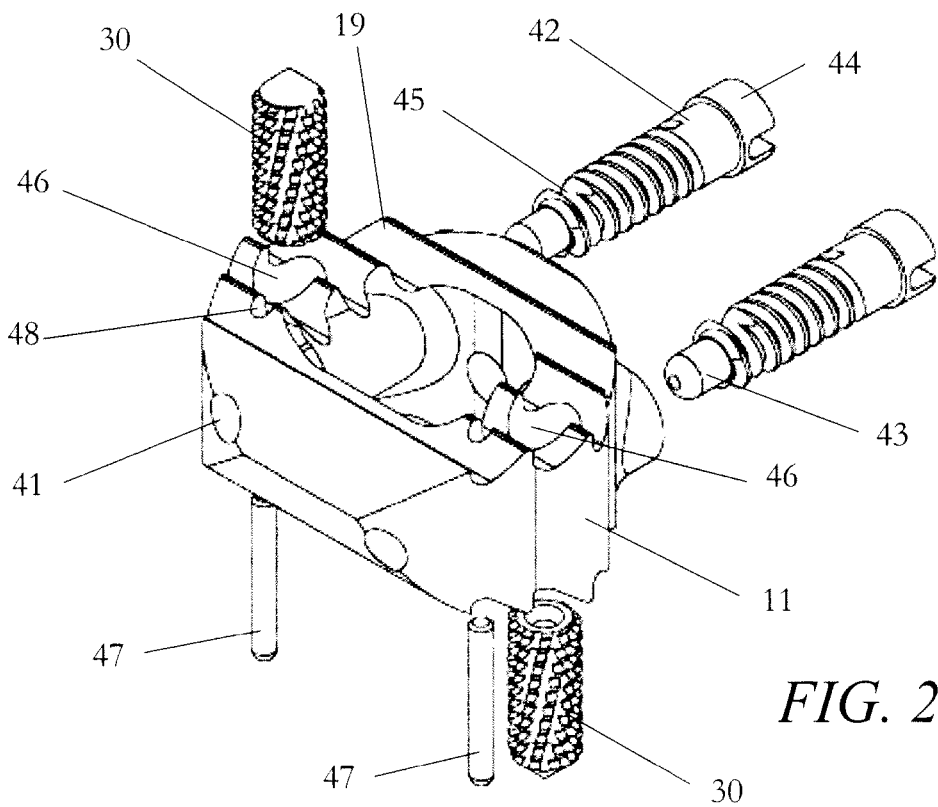
FIG. 2 is an exploded view of an embodiment an embodiment according to the present invention.
Figure 3A:
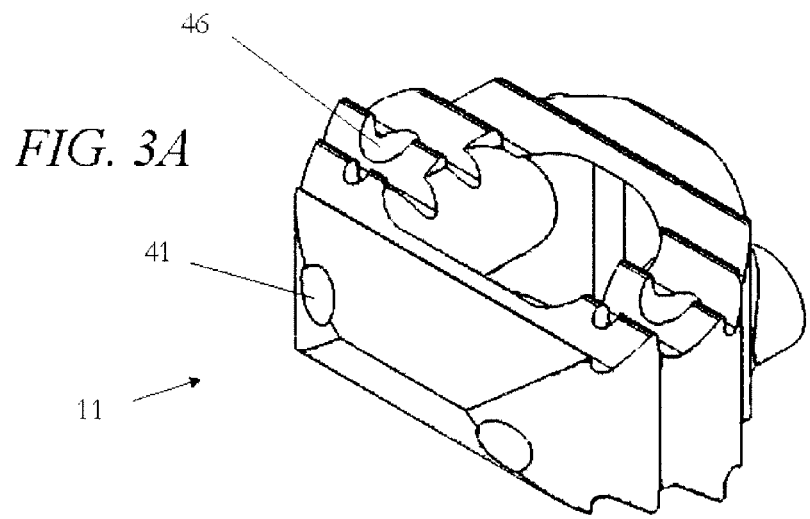
FIG. 3a is a perspective view of an interbody cage according to the present invention.

With reference to FIGS. 1 through 3e and particular reference to FIG. 3c, a preferred embodiment of the fusion cage 10 of the present invention comprises a cage body 11 having a generally irregular annulus shape. The cage body is preferably (but not necessarily) symmetric in overall shape about a central axis 51 (See FIG. 3C) forming left and right halves 12, 14 that are joined at the front 17 and back 15 to form an annular body surrounding a central void 25 extending from upper surface 16 to lower surface 18 (See FIG. 3E). It should be observed that the relative terms "front," "back," "left," "right," "top," or "bottom" are utilized herein to describe the depictions of the invention as provided in the figures and are not necessarily intended to refer to the orientation of the device when implanted nor to limit the disclosure. Further, the term "half" should not be strictly construed to mean "one of two equal parts of a whole" but rather only as one of two approximately equivalent portions of a whole that, taken together do not necessarily constitute the entirety of the whole. In alternate embodiments the central void my be omitted.

Upper surface 16 and lower surface 18 contact the end plates of the vertebra immediately above and below the cage 10 when implanted into the intervertebral space and are generally planar as depicted (not withstanding any surface texturing such as the lateral ridges 19 described below) but need not be so and may be curved or otherwise shaped to provide for an anatomical fit. In a preferred embodiment the height of the cage body 11 is constant such that the upper and lower surfaces 16, 18 are parallel to one another and to the longitudinal axis of the drive mechanism (drive screw) 42 (described below) such that the taper angle α is about 0°. In an alternate preferred embodiment the height of the cage body 11 may taper down from the front 17 to the back 15 to, for example, recreate the normal lumbar or cervical lordosis. In such an embodiment the upper and lower surfaces 16, 18 may converge with a taper angle α of up to about 10° and preferably symmetrically at about +5° on either side of the center line.

Upper and lower surfaces 16, 18 may be further articulated to favor insertion of the cage in one direction while resisting repulsion of the cage. In the depicted embodiment the upper and lower surface 16, 18 are provided with a series of transverse ridges 19 that are asymmetrical, each ridge having a moderate slope on the front edge and a much steeper slope on the back edge such that the ridges permit frontal insertion into the intervertebral space but act as teeth against the vertebral end plates to resist backward expulsion. Surface texturing such as ridges 19 is independent of any tapering of the height of the cage body 11 as described above. The front portion 15 of cage body 11 may also be independently tapered or rounded (FIG. 3F) to ease frontal insertion of the fusion cage 10 into the retracted intervertebral space during surgical implantation without effecting final spinal geometry.

Figure 6:
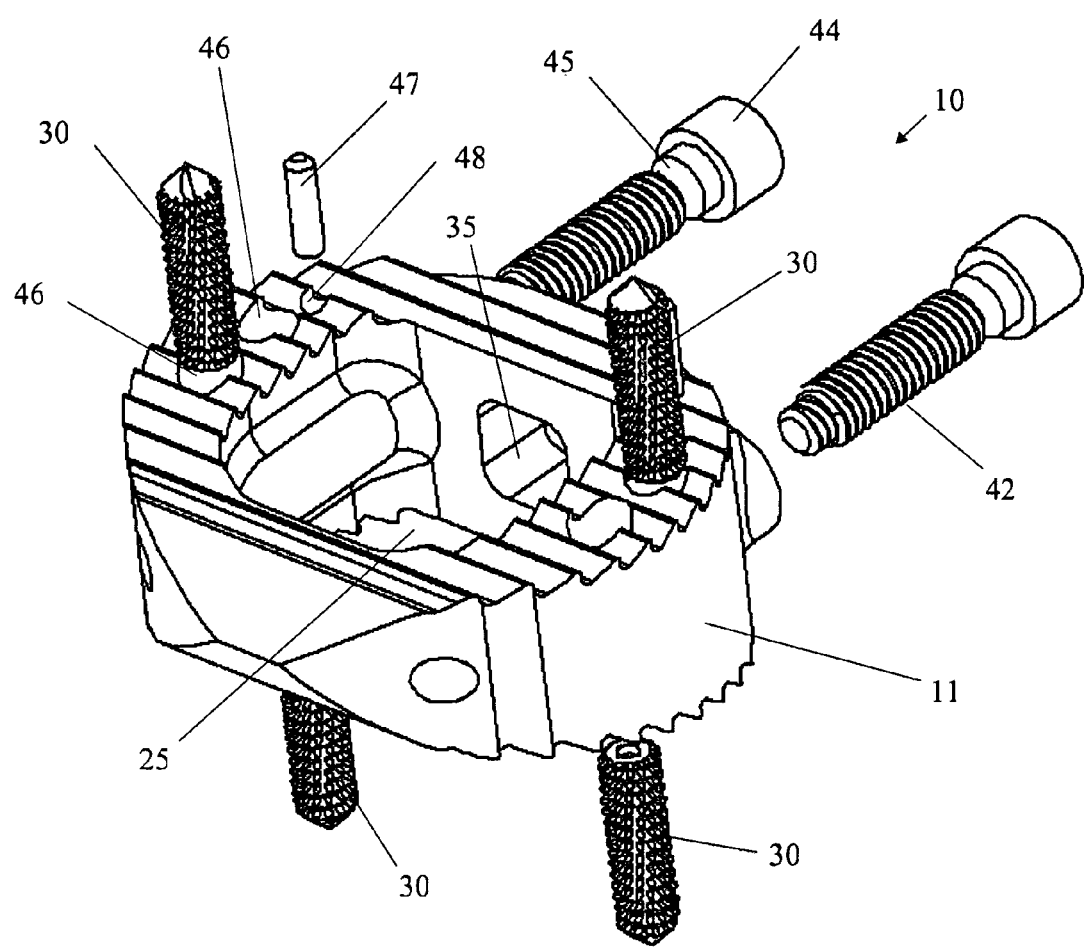
FIG. 6 is an exploded perspective view of an alternate embodiment of the present invention.

With reference to FIG. 3E, cage body 11 is characterized by a plurality of longitudinal channels 46 extending from upper surface 16 to the lower surface 18 in which the pins 30 are housed prior to implantation as described below. In the preferred embodiment of FIG. 2, a single channel 46 is provided in each half 12, 14. The alternate preferred embodiment of FIG. 6 provides two channels 46 in each half (four total) although varying numbers of channels and pin orientations are contemplated in keeping with the present invention.

Figure 3D:
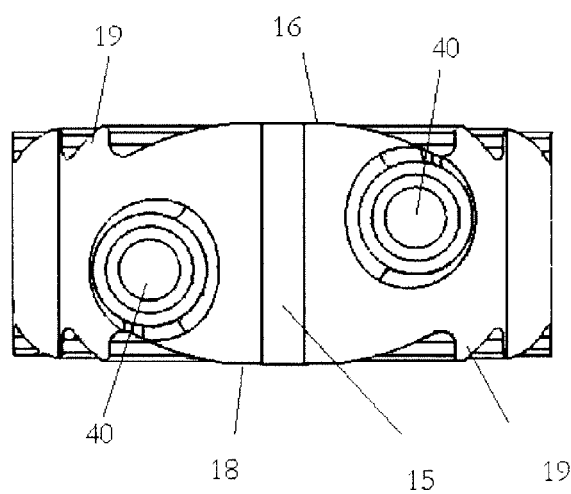
FIG. 3d is an elevation view of an interbody cage according to the present invention.
Figure 3B:
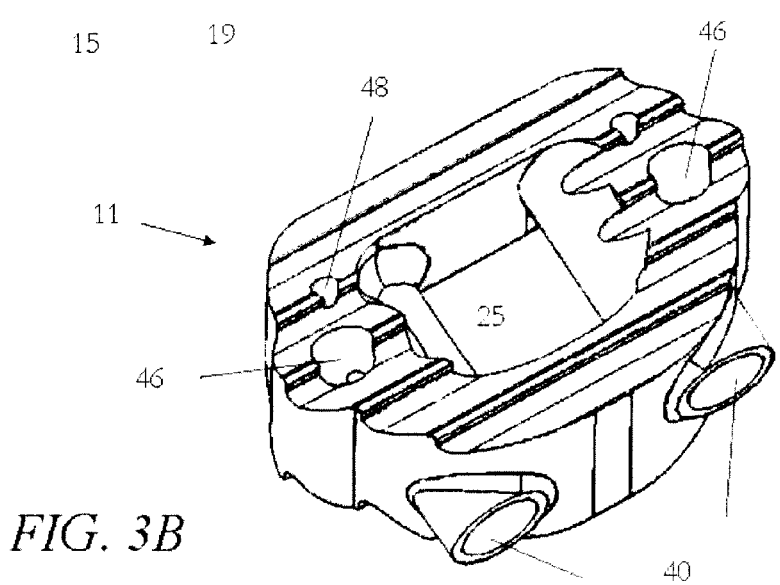
FIG. 3b is a perspective view of an interbody cage according to the present invention.

With further reference to FIGS. 3D, 3E and 3F, halves 12, 14 are each provided with a lateral channel 40 running from front to back through their respective centers. Lateral channels 40 extend through the front of the halves 12, 14 so as to be externally accessible and are preferably substantially orthogonal to the longitudinal channels 46. The center lines of lateral channels 40 and longitudinal channels 46 are off set such that the channels partially intersect within the halves 12, 14. The lateral channel 40 is occupied by a threaded drive screw 42. The longitudinal channel is occupied by a toothed pin 30. The partial intersection of the lateral and longitudinal channels is in such that the pin 30 is engaged by the threads of the drive screw 42 as detailed below.

Cage body 11 can be machined from metallic or polymer materials and is preferably made from an implantable grade polymer thermoplastic that is chemical resistant, able to be sterilized without degradation in mechanical properties or biocompatibility, compatible with X-ray, CT and MRI imaging systems, has low levels of extractables and leachables and displays sufficient stiffness, toughness, and durability. The exemplary embodiment of the cage body 11 of the present invention is machined from implantable grade polyetheretherketone (PEEK) and is provided in a variety of sizes for use at different points along the spinal column or in patients of differing physical size at the discretion of the surgeon. Preferably, fusion cage 10 is provided in 6 mm, 7 mm, 8 mm, and 9 mm heights having a footprint of 11 mm by 14 mm for implantation in the cervical region of the spine and in 9 mm, 11 mm, 13 mm, 15 mm and 17 mm heights with a footprint of either 24 mm by 30 mm or 28 mm by 36 mm for implantation in the lumbar region of the spine. Similarly, fusion cages 10 for cervical implantation are preferably provided with a taper angle of either about 0 or about 5 degrees while fusion cages 10 for lumbar implantation are preferably provided with a taper angle of either about 5 or about 10 degrees.

Figure 4:
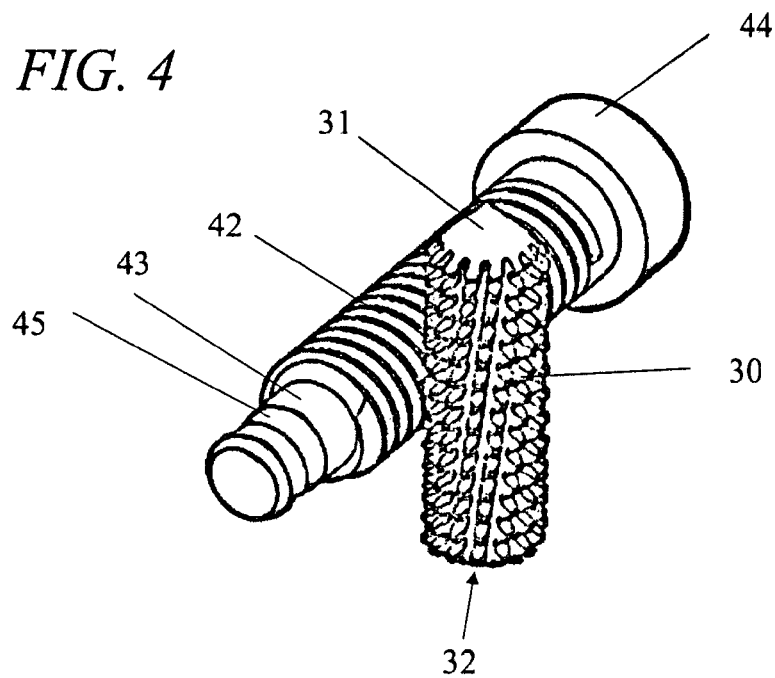
FIG. 4 is a partial perspective view of the drive mechanism of the present invention.
Figure 5:
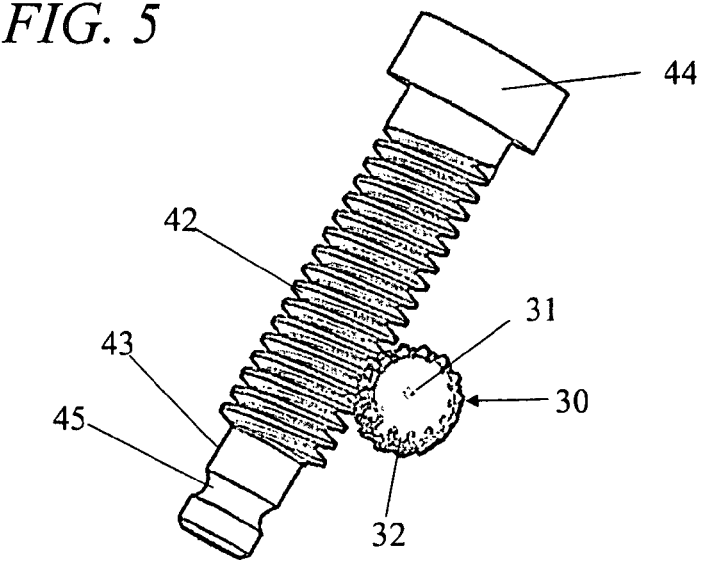
FIG. 5 is a partial perspective view of the drive mechanism of the present invention.

The drive screw 42, depicted in FIGS. 4 and 5 as it would be engaged to the pin 30 but absent the cage body 11, is helically threaded along its length in the manner of a worm and may be single or multiple start and may be further throated to increase engagement with the pin 30. The drive screw 42 is provided with a head 44 that is accessible, when assembled, through the front wall of the cage body 11, the head being configured for engagement with a TORX® wrench or similar surgeon's tool so as to be rotatable within the channel 40. The distal tip 43 of drive screw 42 may be of reduced diameter such that it is rotatably received in a section 41 (FIG. 3F) of channel 40 having a cooperatively reduced diameter. Tip 43 rotates within section 41 under force of the surgeon's tool at head 44 so as to act as a bearing on which the drive screw 42 can rotate within the channel. The distal tip 43 may further be provided with a concave annular ring 45 about its external surface. The ring 45 is engaged by a retainer (pin) 47 (FIG. 2) inserted in a hole 48 perpendicular to the axis of rotation of drive screw 42 which prevents withdrawal of the drive screw 42 without inhibiting rotation. The concave annular ring may alternately be positioned elsewhere along the length of the drive screw 42 such as proximal to head 44 as depicted in FIG. 6.

A plurality of pins 30 is provided, one each, in the vertical channels 46. The pins 30, as best seen in FIGS. 2, 3E, 4 or 5 are provided on substantially the entire length of their exterior surface with a series of radially oriented helically cut (hobbed) teeth 32 in the manner of a worm gear. The helical cut of the teeth 32 (as opposed to the straight cut of spur gear teeth) permit engagement with the threading of the drive screw (see FIGS. 4, 5) such that the pin 31 is caused to rotate in the vertical channel 46 when the drive screw 42 is rotated in the channel 40. It is necessary that the teeth extend the entire length of the pin in order to maintain engagement with the drive screw 42 as the pin is deployed (i.e. translated relative to the drive screw 42). At a minimum, the teeth must extend a distance along the pin 30 equal to the desired depth of deployment into the bone to maintain engagement with the drive screw 42.

In addition to having helically cut teeth 32, substantially the entire length of the surface of pin 30 is cut about its longitudinal axis with external threads though the teeth 32. Simultaneous cutting of teeth 32 and threads on the surface of the pin 30 permits the pin to engage both the drive screw 42 and the internal surface of the longitudinal channel 46 which is cooperatively threaded (tapped) such that rotation of pin within the longitudinal channel 46 (under influence of drive screw 42) advances (translates) the pin 30 out of the longitudinal channel and into the adjacent bone. The pin 30 is further provided with a pointed tip 31 for penetrating the vertebral bone. Tip 31 may form a simple conical taper as depicted or may be provided with a cutting edge to aid penetration of the bone when advanced as described herein. The circular thickness of teeth 32 in the proximal and distal regions of the pin 30 may be increased to limit the advancement of the pin and prevent loss of the pin within the vertebral body due to over advancement.

In a preferred embodiment, the cage 10 is provided with a pair of pins 30 such that one is extended from each half (two total), the pins being oriented to deploy in opposing directions through the upper surface 16 or the lower surface 18. After insertion of the cage 10 into the intervertebral space the pins 30 are advanced such that their distal points pierce and the shaft penetrates the bone of the adjacent vertebra in order to secure the two vertebra in relative proximity to one another and to the graft material retained within central void 25. In the alternate embodiment depicted in FIG. 6 the cage 10 is provided with two pairs of pins 30 such that one pin extends in each direction, both upward and downward from each half 12, 14.

The pins 30 preferably advanced after implantation to penetrate the hard cortical bone of the vertebra and extend into the cancellous bone to prevent both translation and rotation of the cage 10. A surgeon utilizing a cage according to the present invention may thin or remove the hard cortical bone of a portion of the vertebral endplate so as to allow the graft material of the central void 25 to directly contact the cancellous bone thereby facilitating fusion. It is preferred that the upper and lower surfaces 16, 18 of the halves 12, 14 contact cortical bone and that pin 30 extend through and into the cancellous bone to ensure stability and reduce the likelihood of subsidence.

To extend the pins 30 once the cage 10 is positioned to the satisfaction of the surgeon, a tool is inserted to engage and rotate head 44. Rotation of the tool turns the drive screw 42 and the male threads of the drive screw 42 engage the teeth 32 of the pin 30 causing it to rotate within the vertical channel 46. The external threading of the pin 30, engaged to the internally threaded surface of the vertical channel 46, causes the pin 30 to advance out of the cage 10 via the upper or lower surface as the case may be. The increased circular thickness of teeth 32 at the end regions of the pin binds against the drive screw 42 to prevent the pin from being advanced all the way out of the cage 10 to be lost in the bone.

In the preferred embodiment of FIG. 2, a single pin 30 is deployed from each of the left and right halves 12, 14 with one pin advancing from upper surface 16 and the other from lower surface 18. In an alternate preferred embodiment of FIG. 6, each half 12, 14 is provided with a pair of pins 30 within a cooperative pair of vertical channels 46, each pin 30 within a given half being engaged to a single drive screw 42 and configured to simultaneously advance in opposite directions (up/down) in response to rotation of the single drive screw. As also seen in FIG. 6, an aperture 35 may be provided in the cage body to permit packing of the central void 25 with graft material by the surgeon after implantation of the cage 10.

It should be understood that the disclosure may be constructed of a variety of suitable surgical grade materials including stainless steel and titanium as well as composite materials having suitable strength and corrosion resistance properties should such materials be approved for surgical implantation. This application is therefore intended to cover any variations, uses, or adaptations of the invention using its general principles. Further, this application is intended to cover such departures from the present disclosure as come within known or customary practice in the art to which this invention pertains.

We claim:

1. A prosthesis for stabilizing and maintaining space between adjacent bones for promotion of fusion by retained graft material, the prosthesis comprising:
    a spacer body having a top surface, a bottom surface and a perimeter surface joining said top surface and bottom surface, said spacer body further comprising
    at least one lateral channel extending into said spacer body from said perimeter surface; and
    at least one internally threaded longitudinal channel extending from said upper surface or said lower surface and intersecting said lateral channel;
    a drive screw having a head and a first externally threaded surface, said drive screw rotatably mounted in said at least one lateral channel, said head accessible at said perimeter surface so as to be engageable by an externally applied tool for rotation thereof;
    a pin retained in said at least one longitudinal channel, said pin having a pointed distal end and an external surface comprising a plurality of teeth projecting radially therefrom, said plurality of teeth simultaneously defining a first helical thread engaging said externally threaded surface of said drive screw and a second helical thread engaging said internal threading of said longitudinal channel,
    whereby on rotation of said drive screw within said lateral channel, engagement of said first helical thread of said pin with said first externally threaded surface of said drive screw causes said pin to rotate in said longitudinal channel whereby engagement of said second helical thread of said pin with said internally threaded surface of said longitudinal channel causes said pointed distal end of said pin to be advanced out of said longitudinal channel.

2. The prosthesis of claim 1 wherein said spacer body is an annular spacer body having a central void extending from said lower surface to said upper surface and wherein said at least one lateral channel comprises a first lateral channel and a second lateral channel, said first lateral channel positioned on a first side of said central void and said second lateral channel positioned on a second side of said central void.

3. The prosthesis of claim 1 wherein said at least one longitudinal channel extending from said upper surface or said lower surface and intersecting said lateral channel comprises two longitudinal channels.

4. The prosthesis of claim 1 wherein said upper surface and said lower surface are characterized by a plurality of asymmetric transverse ridges.

5. A prosthesis for stabilizing and maintaining space between adjacent vertebra for promotion of fusion by retained graft material, the prosthesis comprising:
    an annular spacer body having a top surface, a bottom surface, a perimeter surface joining said top surface and bottom surface and a central void extending from said top surface to said bottom surface, said spacer body further comprising
    at least one lateral channel extending into said spacer body from said perimeter surface; and
    at least one longitudinal channel extending from said upper surface or said lower surface and intersecting said at least one lateral channel, said longitudinal channel further having an internally threaded surface;
    a drive screw rotatably mounted in each of said at least one lateral channels, said drive screw having a head and an externally threaded surface, said head accessible at said perimeter surface so as to be engageable by an externally applied tool for rotation thereof; and
    a pin rotatably retained in each of said longitudinal channels having a pointed distal end,
        said pin further comprising
        a plurality of teeth projecting radially from an external surface of said pin, said teeth simultaneously defining a first helical thread engaging the first externally threaded surface of said drive screw and a second helical thread, said second helical thread engaging the internal threading of said longitudinal channel;
    wherein rotation of said drive screw within said lateral channel causes said first threaded surface to drive rotation of said pin via said teeth and wherein rotation of said pin advances said pin out of said longitudinal channel by engagement of said second externally threaded surface with said internally threaded surface.

6. The prosthesis of claim 5 wherein said at least one lateral channel comprises a first lateral channel on one side of said central void and a second lateral channel on another side of said central void.

7. The prosthesis of claim 6 wherein said at least one longitudinal channel comprises
    a first longitudinal channel intersecting said first lateral channel; and
    a second longitudinal channel intersecting said second lateral channel.

8. The prosthesis of claim 6 wherein said at least one longitudinal channel comprises
    a first longitudinal channel intersecting said first lateral channel;
    a second longitudinal channel intersecting said first lateral channel;
    a third longitudinal channel intersecting said second lateral channel;
    a fourth longitudinal channel intersecting said second lateral channel.

9. The prosthesis of claim 5 wherein
    said drive screw further comprises an annular ring of reduced diameter; and
    wherein said prosthesis further comprises a retainer engaged within said annular ring to prevent withdrawal of said drive screw without impeding rotation thereof.

10. The prosthesis of claim 5 further comprising an aperture through said perimeter surface into said central void for in-situ introduction of said graft material.

11. The prosthesis of claim 5 wherein said at least one longitudinal channel comprises a first longitudinal channel and a second longitudinal channel.

12. The prosthesis of claim 5 having a taper angle of about 0° to about 10°, symmetric about a center line.

13. The prosthesis of claim 5 wherein said upper surface and said lower surface are characterized by a plurality of asymmetric transverse ridges.

14. A prosthesis for stabilizing and maintaining space between adjacent vertebra for promotion of fusion by retained graft material, the prosthesis comprising:

an annular spacer body having a first half and a second half joined to encircle a central void, said central void extending from a top surface of said annular spacer body to a bottom surface of said annular spacer body, each of said first half and said second half further comprising a lateral channel extending into said annular spacer body between said upper surface and said lower surface; and at least one internally threaded longitudinal channel extending from said upper surface or said lower surface and intersecting said lateral channel;

a worm rotatably mounted in each of said lateral channels, said worm having a head engageable by an externally applied tool for rotation thereof;

a pin rotatably retained in each of said longitudinal channels having a pointed distal end and an opposing proximal end, said pin having an external surface extending substantially the length of the pin further comprising worm gear teeth, said teeth engaging said worm, the teeth of said proximal end having an increased circular thickness; and helical threads, said helical threads engaging the internal threading of said longitudinal channel;

wherein rotation of said worm within said lateral channel causes rotation of said pin by engagement with said teeth and wherein rotation of said pin causes translation of said pointed distal end of said pin out of said longitudinal channel by engagement of said threads with said internally threaded surface, the translation of said pointed distal end being limited by engagement of said teeth of said proximal end of said pin with said worm.

\* \* \* \* \*